(12) United States Patent
Patterson

(10) Patent No.: US 10,285,742 B1
(45) Date of Patent: May 14, 2019

(54) BONE MANIPULATOR SYSTEM AND METHOD

(71) Applicant: Avanti Orthopaedics, LLC, Newark, DE (US)

(72) Inventor: John Douglas Patterson, Newark, DE (US)

(73) Assignee: Avanti Orthopaedics LLC, Newark, DE (US)

(*) Notice: Subject to any disclaimer, the term of this patent is extended or adjusted under 35 U.S.C. 154(b) by 0 days.

(21) Appl. No.: 16/016,299

(22) Filed: Jun. 22, 2018

(51) Int. Cl.
| | |
|---|---|
| *A61B 17/56* | (2006.01) |
| *A61B 17/80* | (2006.01) |
| *A61B 17/00* | (2006.01) |

(52) U.S. Cl.
CPC ........ *A61B 17/8019* (2013.01); *A61B 17/808* (2013.01); *A61B 17/8052* (2013.01); *A61B 2017/0046* (2013.01); *A61B 2017/00407* (2013.01); *A61B 2017/564* (2013.01)

(58) Field of Classification Search
CPC .............. A61B 17/808; A61B 17/8004; A61B 17/8014; A61B 17/8019; A61B 17/8052; A61B 17/7074; A61B 17/56
USPC ................................................ 606/281, 86 B
See application file for complete search history.

(56) References Cited

U.S. PATENT DOCUMENTS

| | | | |
|---|---|---|---|
| 7,473,257 B2 | 1/2009 | Knopfle et al. | |
| 8,105,329 B2 | 1/2012 | Brumfield | |
| 8,167,891 B2 | 5/2012 | Terres et al. | |
| 8,585,742 B2 | 11/2013 | Windolf | |
| 8,668,699 B2 | 3/2014 | Thomas et al. | |
| 8,834,485 B2 | 9/2014 | Kave | |
| 9,113,969 B2 | 8/2015 | Niederberger et al. | |
| 9,345,463 B2 | 5/2016 | Butters et al. | |
| 9,351,773 B2 | 5/2016 | DiDomenico et al. | |
| 9,402,665 B2 | 8/2016 | Medoff et al. | |
| 9,597,130 B2 | 3/2017 | Pappalardo et al. | |
| 9,943,348 B2 | 4/2018 | Schelling | |
| 2007/0173842 A1 | 7/2007 | Abdou | |
| 2007/0270850 A1* | 11/2007 | Geissler | A61B 17/15 606/326 |
| 2015/0374425 A1 | 12/2015 | Hashmi et al. | |

* cited by examiner

*Primary Examiner* — Si Ming Ku
(74) *Attorney, Agent, or Firm* — Invention To Patent Services; Alex Hobson

(57) ABSTRACT

A bone manipulator system incorporates a bone manipulator and bone plate that enables two degrees of motion to position a fractured bone, including axial and lateral translation of a bone portion. The bone manipulator system incorporates a bone plate having a plurality of apertures and a bone manipulator having a fastener-arm and a foot-arm for engagement with the bone plate. The fastener coupler of the fastener-arm is configured for rotational engagement with a fastener inserted through one of the apertures of the bone plate and secured into the bone thereunder. The foot-arm has a flared foot end for engagement with a separate aperture of the bone plate. The fractured bone is manipulated by movement of the bone plate by the flared foot end while the bone plate slides and/or rotates about the fastener in the slotted aperture.

8 Claims, 12 Drawing Sheets

BONE MANIPULATOR SYSTEM AND METHOD

BACKGROUND OF THE INVENTION

Field of the Invention

This application is directed to a bone manipulator system incorporating a bone manipulator and bone plate that enables two degrees of motion to position a fractured bone, including axial and lateral translation of a bone portion.

Background

Bone plates are commonly used to secure fractured bones together to promote healing and restore proper orientation. Fractured bones however are seldom in alignment and a fractured bone portion may be displaced axially from the rest of the fractured bone to produce a fracture gap or a compressed region, may be displaced laterally from a length axis of the fractured bone and/or may be rotated out of position. Surgeons routinely have difficulty positioning the fracture bone while trying to secure a bone plate. Positioning a fracture bone with a minimal fracture gap proper alignment can improve the rate of healing and reduce future complications.

SUMMARY OF THE INVENTION

The invention is directed to a bone manipulator system incorporating a bone manipulator and bone plate that enables two degrees of motion to position a fractured bone, including axial and lateral translation of a bone portion. The bone manipulator system may be used for translation, compression and/or distraction of a fractured bone. A bone manipulator system comprises a bone plate having a plurality of apertures and a bone manipulator having a fastener-arm and a foot-arm for engagement with the bone plate. The fastener coupler of the fastener-arm is configured to engage with a fastener inserted through one of the apertures of the bone plate and the foot-arm has a flared foot end for engagement with an aperture of the bone plate. The foot arm may be inserted into an aperture and the flared foot end may extend just below the bone surface of the bone plate. The fastener-arm and foot-arm are coupled to the handles of the bone manipulator to enable movement of the foot-arm with respect to the fastener-arm. For example, the handles may be squeezed to spread the foot-arm from the fastener-arm. The bone manipulator may comprise a handle lock to secure the handles in a fixed position. A surgeon may squeeze the handles to manipulate the bone plate and the fractured bone coupled thereto and then lock the handles in position to allow the surgeon to securely fix the bone plate to the fractured bone.

An exemplary fastener-arm comprises a fastener coupler having a cavity for extending over a fastener head. An exemplary fastener coupler has a domed shaped cavity that enables the bone manipulator to be translated or rotated about the fastener while maintaining engagement. The opening to the cavity may have a diameter larger than the diameter of the fastener head and the cavity may tapper from the opening to allow engagement with fastener head of various diameters. The diameter of the opening of the cavity of the fastener coupler may be slightly larger than the head of a fastener, such as a screw head, and may be about 3 mm or greater, about 5 mm or greater, about 10 mm or greater, about 20 mm or greater, or any dimension between and including the opening diameter values provided, such as from about 3 mm to 20 mm. The cavity may be conical or spherical in shape, wherein it trappers in dimension from the opening to the cavity. The inside cavity may be domed shaped to allow smooth pivoting and rotation of the fastener coupler when engaged over the head of a fastener and may have a radius equal to half of the diameter cavity opening, as described herein. The inside surface of the cavity may be circular in cross-section along the length axis of the fastener-arm from the opening and the cross-sectional diameter of the inside surface may taper from the opening. A circular cross-sectional of the cavity along the length and the tapering cavity enables the fastener coupler to extend over the head of a fastener and rotate while maintaining engagement or contact with the fastener head.

An exemplary flared foot end configured on the extended end of the foot-arm tapers in dimension from the extended end toward the foot arm. The flared foot end may have a tapering rod shape, wherein the extended end is circular having a diameter and this diameter tapers from the extended end, conical in shape. The flared foot angle may be about 40 degrees or more, about 55 degrees or more, about 70 degrees or more, about 90 degrees or more and any range between and including the flared foot angles provided. If the flared foot angle is too large it may cause the flared foot to lift the bone plate from the bone which is not desired and a foot with no flare may make it difficult to secure the foot in position. The flared foot end may have a tapered portion between the flared foot end and the foot arm. The tapered portion may taper from the foot-arm to the flared foot end. This tapered portion may allow better positioning of and manipulation of the flared foot end within an aperture.

The bone manipulator may comprise a coupler that couples the handles to the fastener-arm and foot-arms. The coupler may be a pivot whereby one of the handles is coupled with one of the arms and the other handle is coupled with the other arm. A bone manipulator may comprise a handle lock to secure the handle in position. Preferably, the handle lock automatically locks the handles in position upon manipulation of the handles. The handles may be squeezed and the positioning lock may secure the handles in the most compressed position of the handles. A ratcheting mechanism may allow the handles to move in one direction but prevent movement in the opposing direction. The ratcheting mechanism may have a release to allow movement in the restricted direction however and this may be a manual release. The handles may be configured to move toward or away from each other, depending on the type of procedure being performed. In most cases, the handles will be configured to move toward each other and this may cause the two arms, the fastener-arm and foot-arm, to spread apart. However, like scissors, squeezing of the handles may retract a gap between the arms.

An exemplary handle lock may comprise a ratcheting extension that extends from one of the handles and is coupled with the other handle. The ratcheting extension may have a plurality of teeth having a locking portion and a slide portion. The plurality of teeth may extend through or over a latch whereby manipulation of the handles moves the ratcheting extension and the slide portion of the teeth over the latch and when the handles are released, the locking portion of one of the teeth engages with the latch to secure the handle in a fixed position. A locking portion may also comprise a latch and ratcheting assembly that are configured around the coupler or pivot of the two handles, much like a ratcheting wrench.

The bone manipulator system may be used to reposition a fractured bone, whereby a portion of the fractured bone, or fractured portion is moved axially along the length axis of the bone to compress or distract a fracture gap or compressed region, respectively, moved laterally or translated orthogonally with respect to the length axis of the bone to realign the bone portion and/or rotated to realign the bone portions. The bone manipulator system, and in particular, the fastener coupler that is rotatably engaged with the fastener head in a slotted aperture, enables two degrees of freedom. The bone manipulator system may utilize a bone plate with a first aperture that is a slotted aperture. A fastener may be inserted through the slotted aperture and the bone plate may be manipulated with the flared foot end in a second aperture of the bone plate to move the bone plate along the length of the slotted aperture or rotate the bone plate around the fastener within the slotted aperture. Combining these to motions enables lateral movement of a bone portion coupled to the bone plate wherein the plate is both rotated about the fastener within the slotted aperture and moved axially along the length of the slotted aperture. The fastener coupler of the fastener arm is configured for rotational engagement with the head of a fastener.

In an exemplary embodiment, a bone manipulator system is used to distract a compressed region of a bone fracture, wherein a first and second bone portion have been compressed into each other along a fracture or overlap to some degree. In this embodiment and method, the bone manipulator system utilizes a bone plate with first slotted aperture and second aperture configured on opposing sides of a bone fracture. A fastener is inserted through the slotted aperture and the fastener coupler is configured over the head of the fastener. The flared foot end is then inserted into the second aperture and moved away from said fastener to distract the compressed region of a bone fracture, whereby the slotted aperture slides around the fastener.

In an exemplary embodiment, a bone manipulator system is used to retract a fracture gap, wherein a first and second bone portion have been separated from each other along a fracture. In this embodiment and method, the bone manipulator system utilizes a bone plate with first slotted aperture and second aperture configured on the same side of a bone fracture, or over a first bone portion. The first slotted aperture is configured more proximal to the bone fracture than the second aperture. The bone plate extends across the fracture over a second bone portion, which may be a bone fragment, or smaller portion of the bone, and is coupled to the second bone portion, such as by a fastener extending through an aperture in the bone plate. The fastener coupler is engaged with the fastener in the slotted aperture and the flared foot end in inserted into the second aperture and moved away from the fastener in the slotted aperture to move the bone plate and the second bone portion attached thereto toward the fracture to reduce the fracture gap. Again, the bone plate slides around the fastener in the slotted aperture to make this possible. This method reduces the fracture gap and moves the second bone portion axially along the length axis of the bone.

In an exemplary embodiment, a bone manipulator system is used to translate a second bone portion laterally. The method involves the steps of the preceding paragraph and the second bone portion is moved laterally by rotation about the fastener in the slotted aperture and movement axially along the length axis of the slotted aperture. Note that the length axis of the slotted aperture may be initially configured at some offset angle to the length axis of the bone to enable rotation of a bone portion back into alignment while at the same time aligning the bone plate with the length axis of the bone. This technique may enable the required translation of the bone portion and configure the bone plate in favorable position for supporting the fractured bone.

The summary of the invention is provided as a general introduction to some of the embodiments of the invention and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
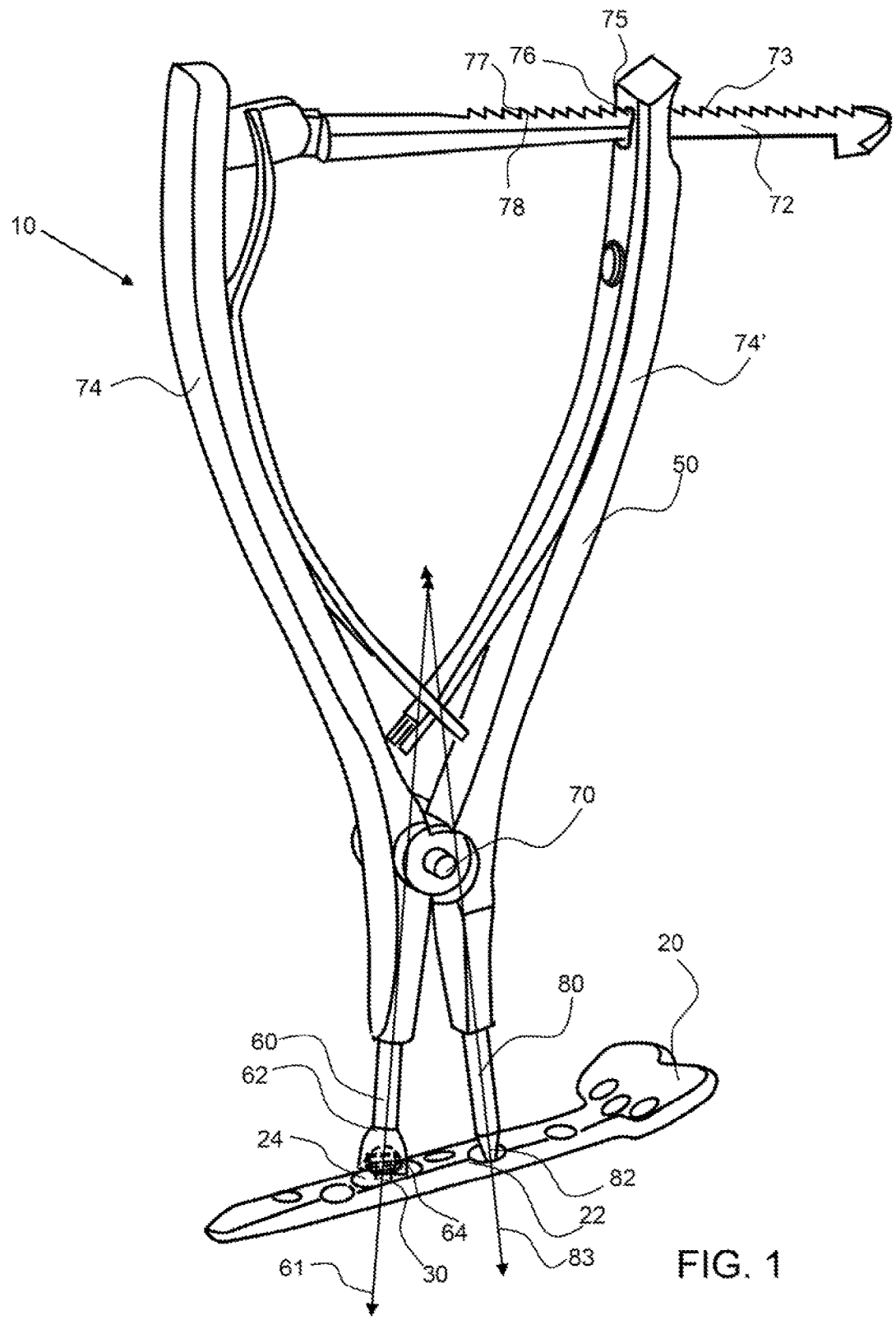
FIG. 1 shows an exemplary bone manipulator having a fastener-arm and a foot-arm engaged with a bone plate.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary bone manipulator system 10 comprises a bone manipulator 50 having a fastener-arm 60 and a foot-arm 80 engaged with a bone plate 20. The fastener-arm has a length axis 61 and the foot-arm has a length axis 83. The foot-arm and fastener-arm extend from the coupling 70, whereby squeezing of the handles 74, 74' spreads the foot-arm and fastener-arm apart. A handle lock 75, to secure the handles in a fixed position, comprises a ratcheting extension 72 having a plurality of teeth 73 that will slide through or over a positioning latch 76 as the handles are squeezed. The teeth have a locking portion 77 that engages the latch and a slide portion 78 that slides over the latch when the handles are squeezed together. When the handles are released, the position will be held by a tooth or teeth engaged with the handle lock 75. The fastener-arm 60 has a fastener coupler 62, or dome coupler 64, configured over a fastener 30 in a slotted aperture 24 and the foot-arm has a flared foot end 82 configured within an aperture 22 of the bone plate 20. The fastener in the slotted aperture extends through the aperture and partially within a bone. The slotted aperture 24 allows the bone plate to move with respect to bone to enable manipulation of the bone with respect to the bone plate to compress or distract a fracture and/or translate a fractured portion of the bone.

Figure 2:
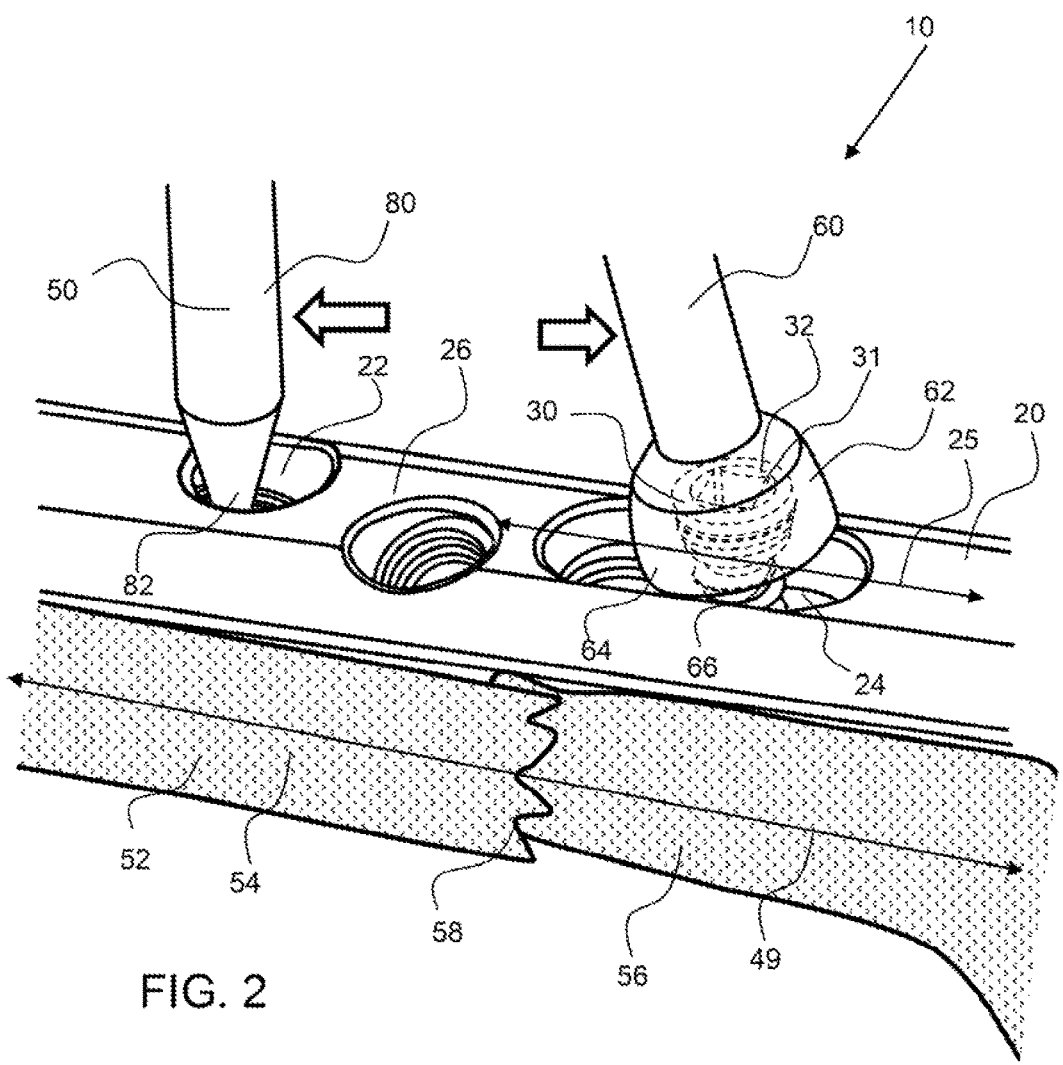
FIG. 2 shows a perspective view of a portion of an exemplary bone manipulator engaged with a bone plate to distract a compressed region of a fractured bone.
Figure 3:
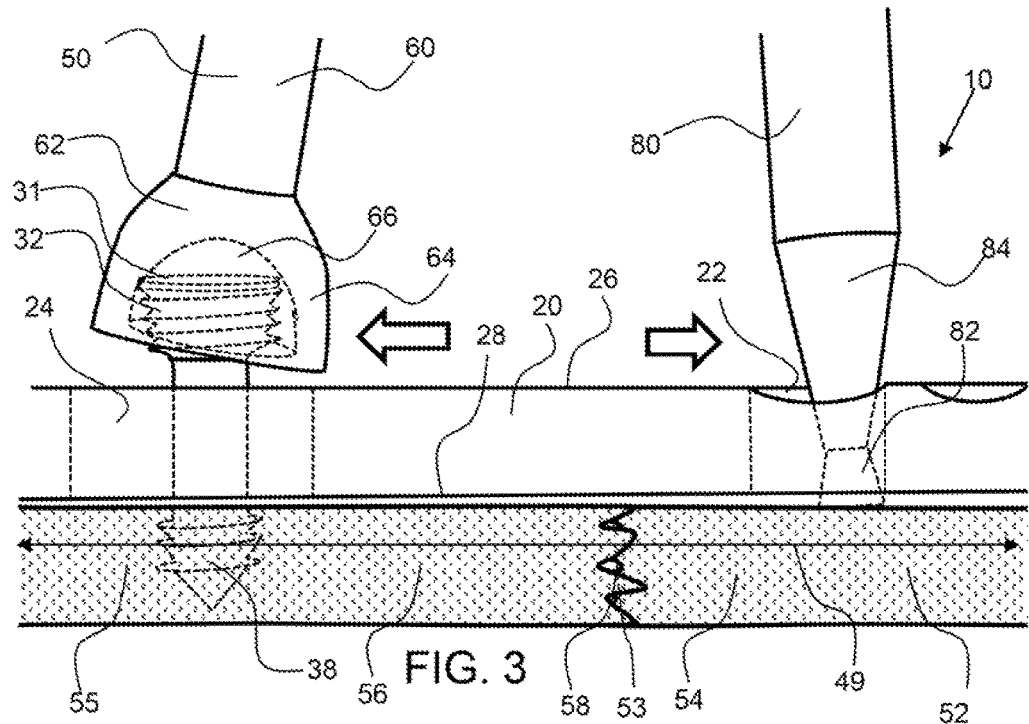
FIGS. 3 and 4 show a side view of an exemplary bone manipulator system distracting a fractured bone.
Figure 4:
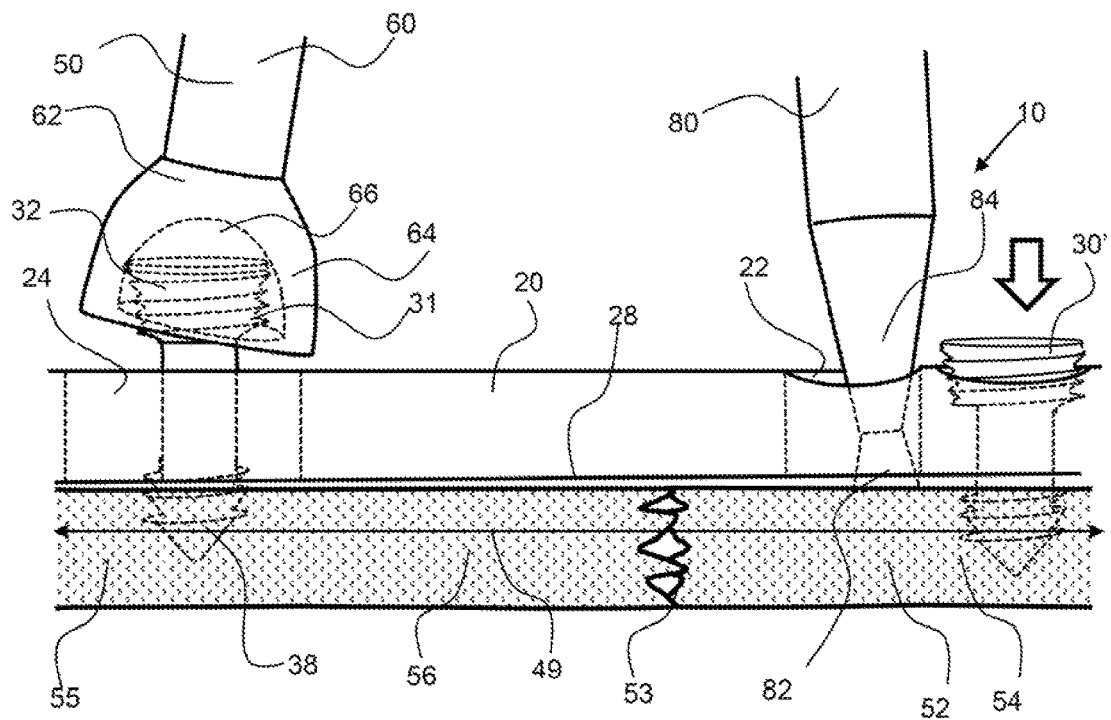
Figure 5:
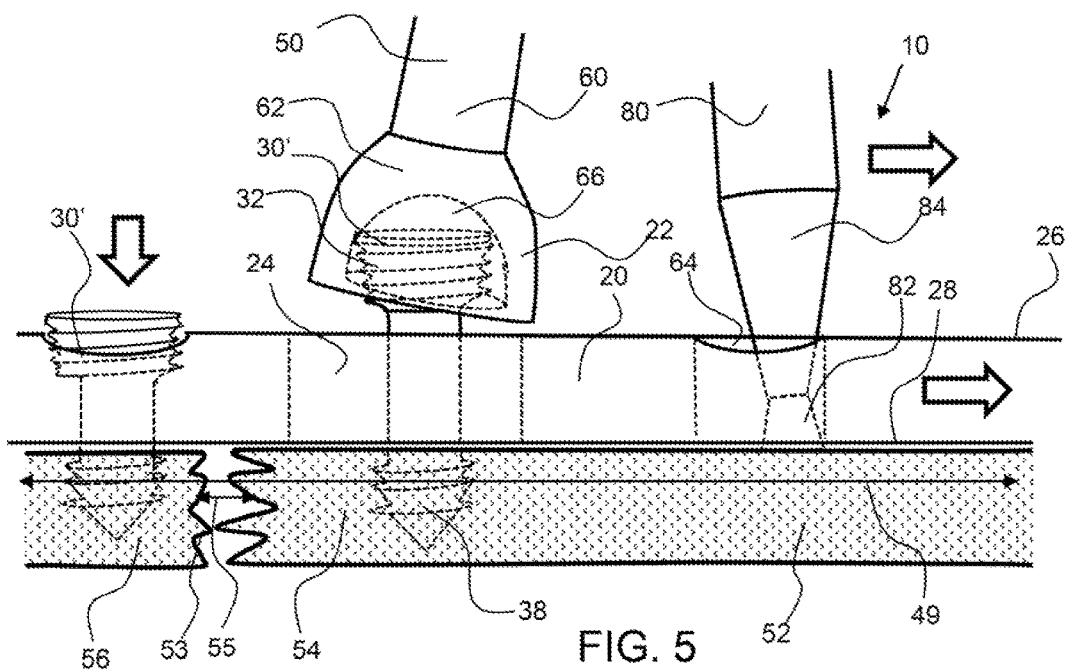
FIGS. 5 and 6 show a side view of an exemplary bone manipulator system compressing a fractured bone to reduce the facture gap.

Referring now to FIGS. 2 to 4, an exemplary bone manipulator system 10 comprises a bone manipulator 50 engaged with a bone plate 20 to distract a fractured bone 52. The fastener-arm 60 has a fastener coupler 64 configured over a fastener 30 in a slotted aperture 24 and the foot-arm 80 has a flared foot end 82 configured within an aperture 22 of the bone plate 20. The slotted aperture has a length axis 25 that generally aligned with the length axis of the bone. The fastener 30, such as a screw 32, extends through the slotted aperture and into the second bone portion 56. The fastener head 31 is elevated from the top surface 26 of the bone plate 20 to allow the fastener coupler 64 to extend around the fastener head for rotational engagement of the bone manipulator about the fastener head. The bone plate 20 has a thickness from the top surface 26 to the bone surface 28. The fracture bone 52 has a compressed region 58, wherein the first bone portion 54 and second bone portion 56 overlap or are compressed into each other. The bone manipulator handles may be squeezed to spread the fastener-arm 60 from the foot-arm 80 to distract the fractured bone, as indicated by the bold arrows. After the bone is distracted to reduce the compressed region, fasteners, such as fastener 30' may be inserted through the apertures of the bone plate to secure the bone in position and to the bone plate, as shown in FIG. 4. Also, screw 32 may be further advanced into the bone to secure it firmly to the bone plate, wherein the bone threads 38 of the fastener are advanced into the bone.

Figure 6:
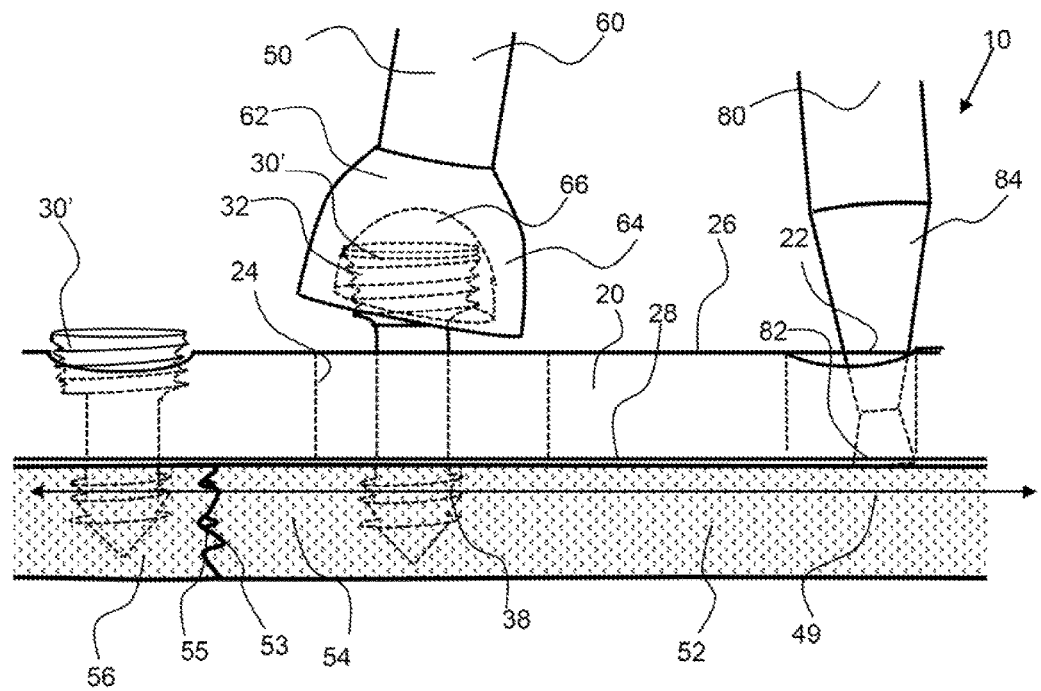
Figure 7:
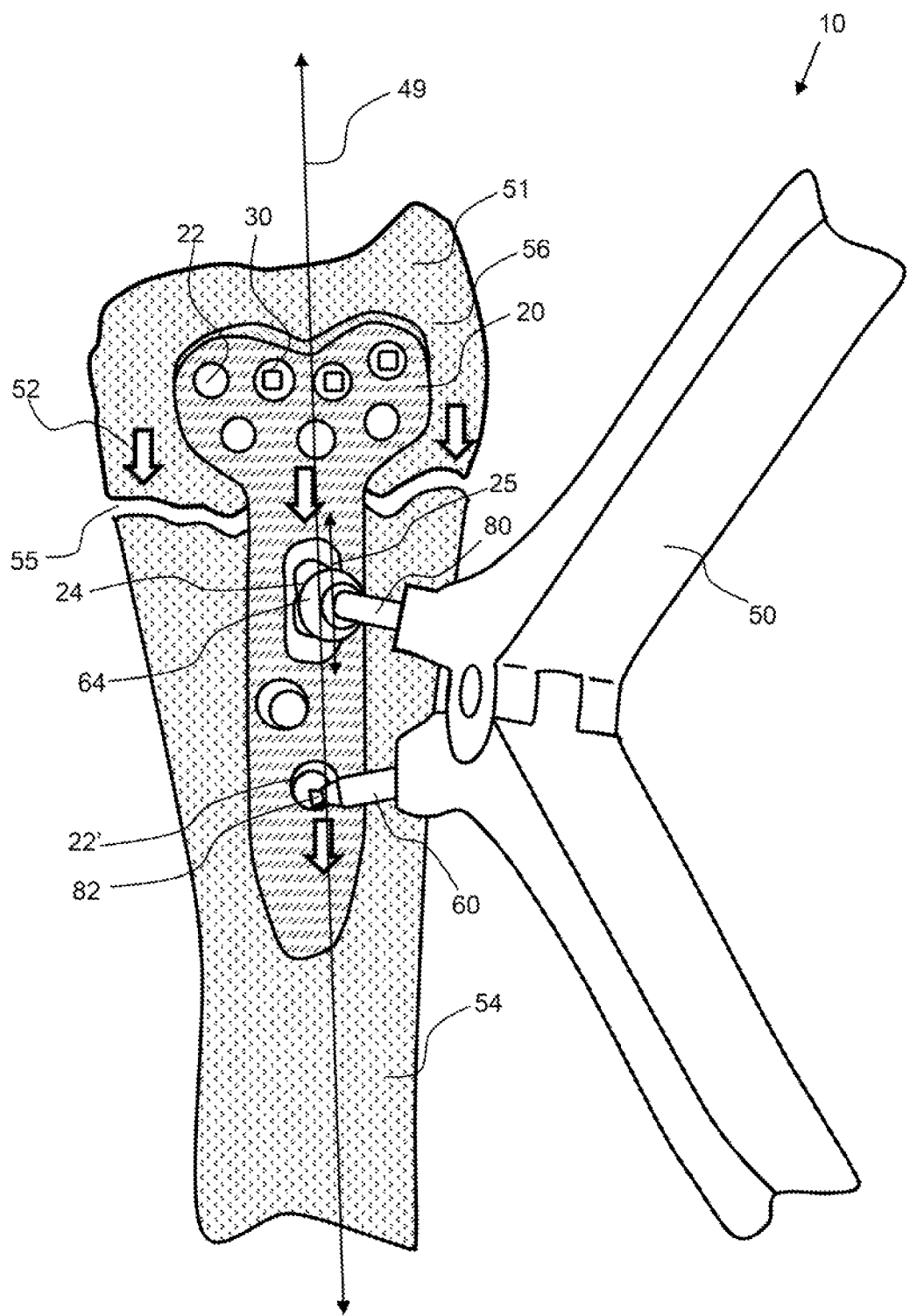
FIGS. 7 and 8 show a top view of an exemplary bone manipulator system compressing a fractured bone to reduce the facture gap.
Figure 8:
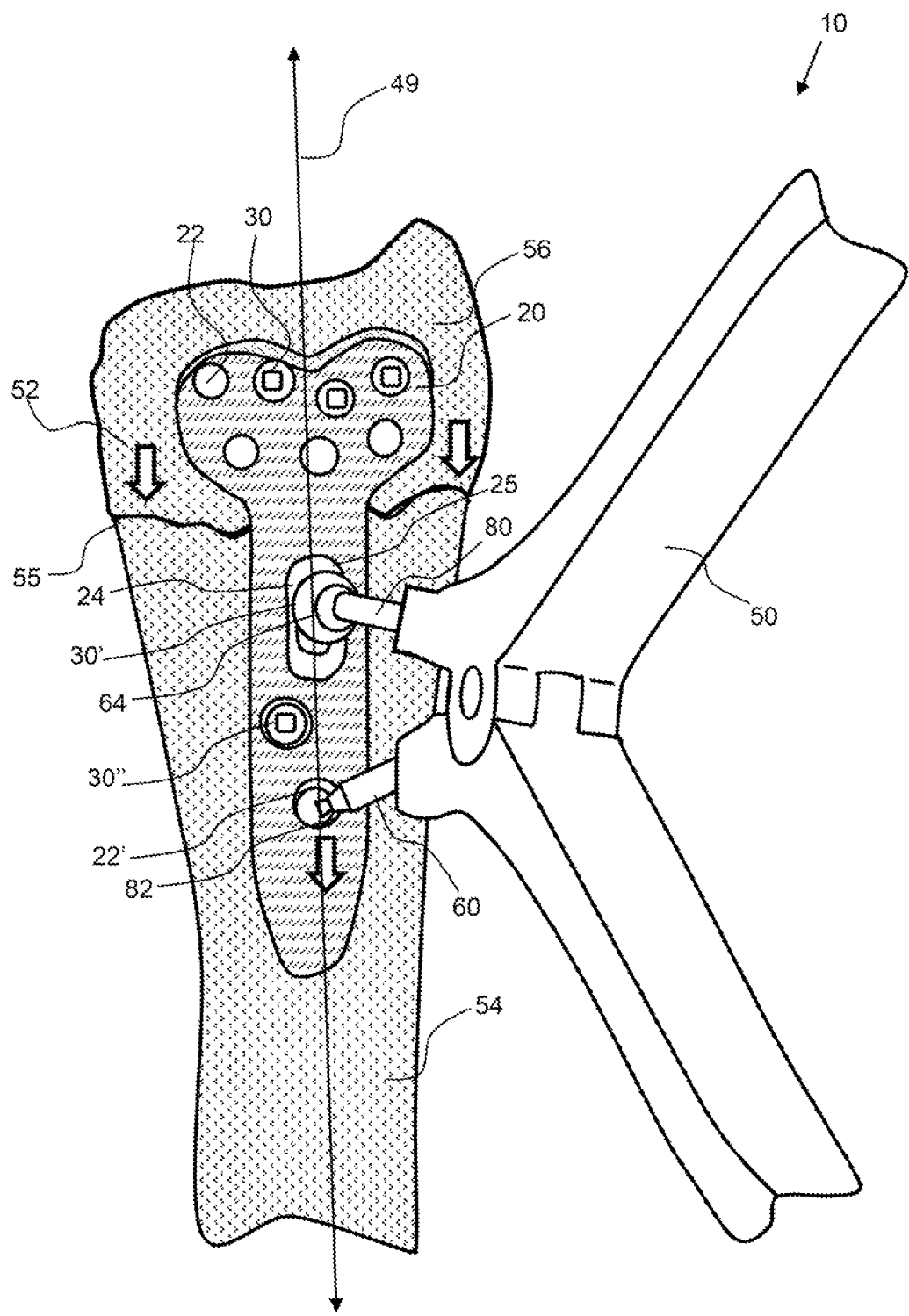

Referring now to FIGS. 5 to 8, an exemplary bone manipulator system 10 comprises a bone manipulator 50 engaged with a bone plate 20 to compress a fractured bone 52. The fastener-arm 60 has a fastener coupler 62, or dome coupler 64, configured over a fastener 30, such as a screw 32, in a slotted aperture 24 and the foot-arm 80 has a flared foot end 82 configured within an aperture 22 of the bone plate 20. The flared foot end engages with the bottom surface 28 of the bone plate to secure the flared foot end to the bone plate. The fracture gap 55 between the first bone portion 54 and the second bone portion 56 is reduced by translation of the bone plate as indicated by the bold arrows. The fastener 30 extends through the slotted aperture and into the first bone portion 54. The bone manipulator handles may be squeezed to spread the fastener-arm 60 from the foot-arm 80 to compress the fractured bone, as indicated by the arrows in FIGS. 5 and 7. The foot-arm 80 moves the bone plate and the second bone portion 56 coupled to the bone plate by the fastener 30'. The bone plate slides over the fastener 30 in the slotted aperture 24 to reduce the fracture gap 55, as shown in FIGS. 6 and 8. This may be a substantially axial translation of the second bone portion 56 along the length axis of the bone 49, as shown in FIGS. 7 and 8. After the fractured bone is compressed, fasteners, such as fastener 30", as shown in FIG. 8 may be inserted through the apertures of the bone plate to secure the bone in position and to the bone plate. The fastener in the slotted aperture may also be further advanced to secure the fastener and bone plate together.

Figure 9:
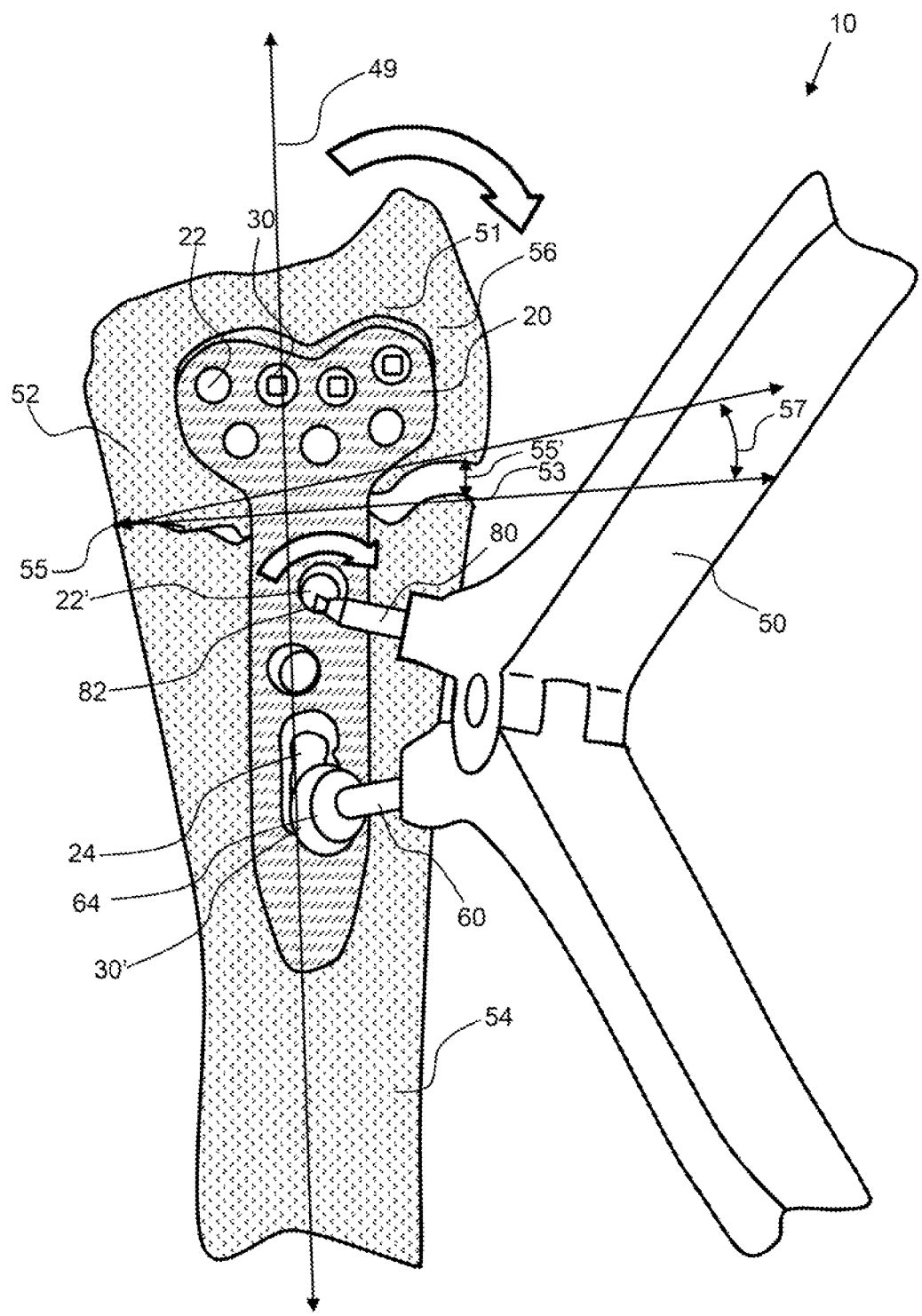
FIGS. 9 and 10 show a top view of an exemplary bone manipulator system rotating a fractured bone to realign the bone across the fracture.
Figure 10:
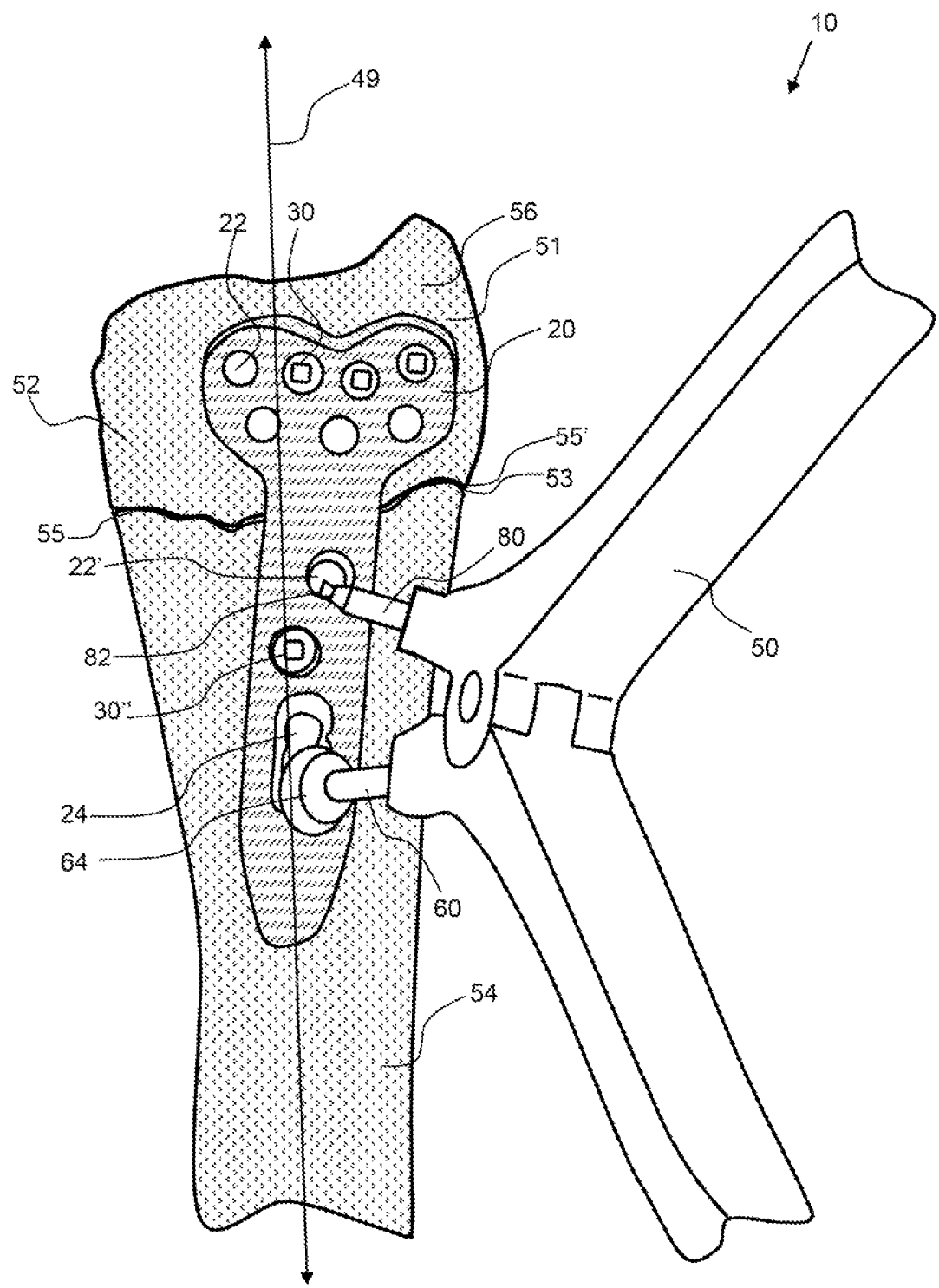

As shown in FIGS. 9 and 10, an exemplary bone manipulator system 10 comprise a bone manipulator 50 that can engage with a bone plate 20 to rotate a displaced fractured bone to realign the bone across the fracture 53. As shown in FIG. 9, a fracture bone is displaced or rotated out of alignment and has a fracture gap having a fracture gap angle 57. The fracture gap 55' is larger on one side of the fracture 53 than, the fracture gap 55 on the opposing side. Note that the bones may be compressed on one side and have a fracture gap on the opposing side. The exemplary bone manipulator may be used to realign the bone. One or more fasteners 30 may be configured through apertures 22 in the bone plate 20 and secured into the second bone portion 56 of the fractured bone 52. The domed coupler 64 of the fastener-arm 60 may be configured over a fastener 30' that extends through an aperture in the bone plate and into the first portion 54 of the fracture bone. The flared foot end 82 of the foot-arm 80 is inserted in a second aperture of the bone plate, such as on that is more proximal to the fracture than the domed coupler 64 but over the first bone portion 54. The bone manipulator can be rotated to manipulate the second bone portion 56 of the fracture bone 52 with respect to the first bone portion 54 to reduce the facture gap and align the bone. A fastener 30" may be inserted through an aperture in the first bone portion 54 to secure the manipulated fractured bone in position and to the bone plate, as shown in FIG. 10.

Figure 11:
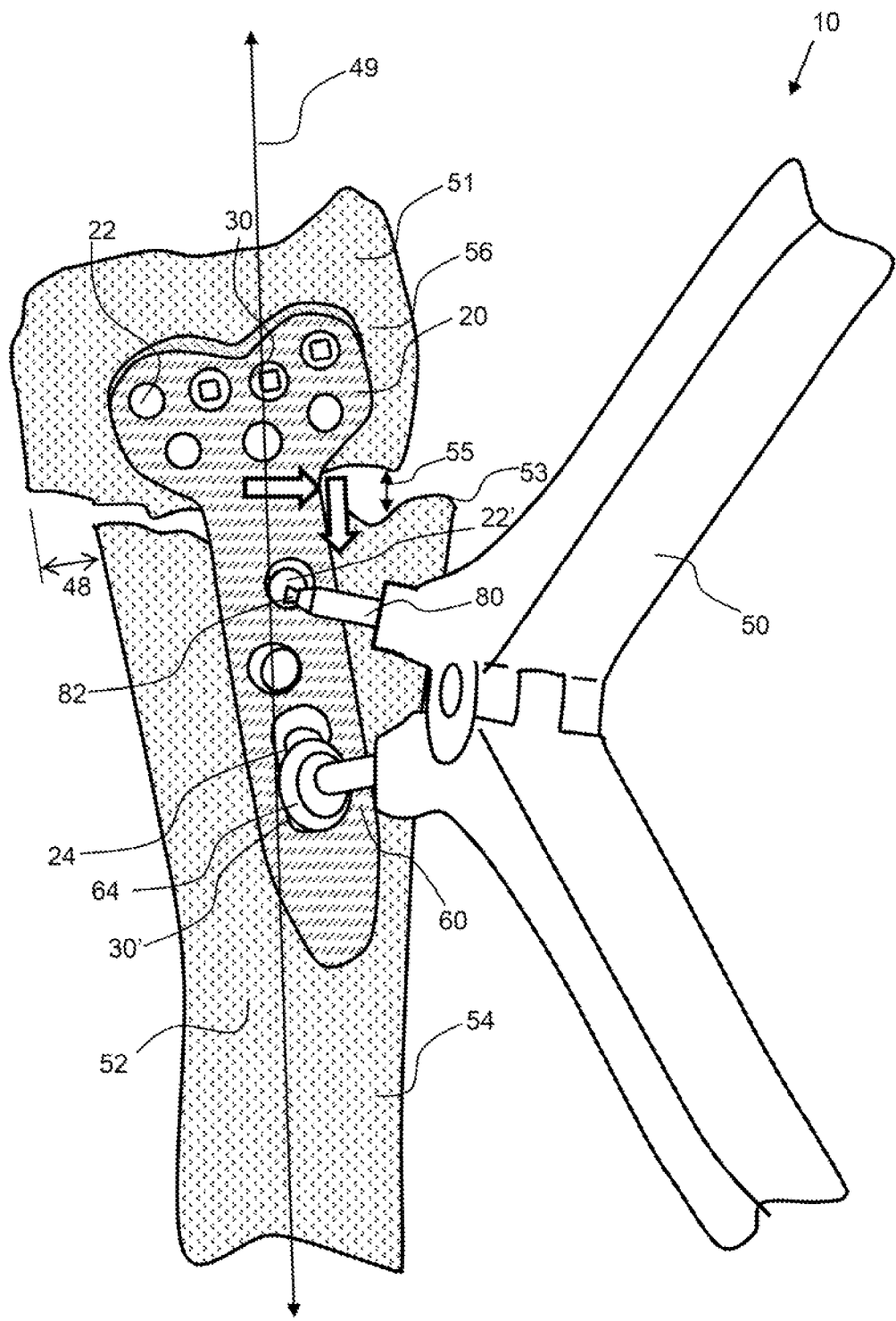
FIGS. 11 and 12 show a top view of an exemplary bone manipulator system translating a bone fracture.
Figure 12:
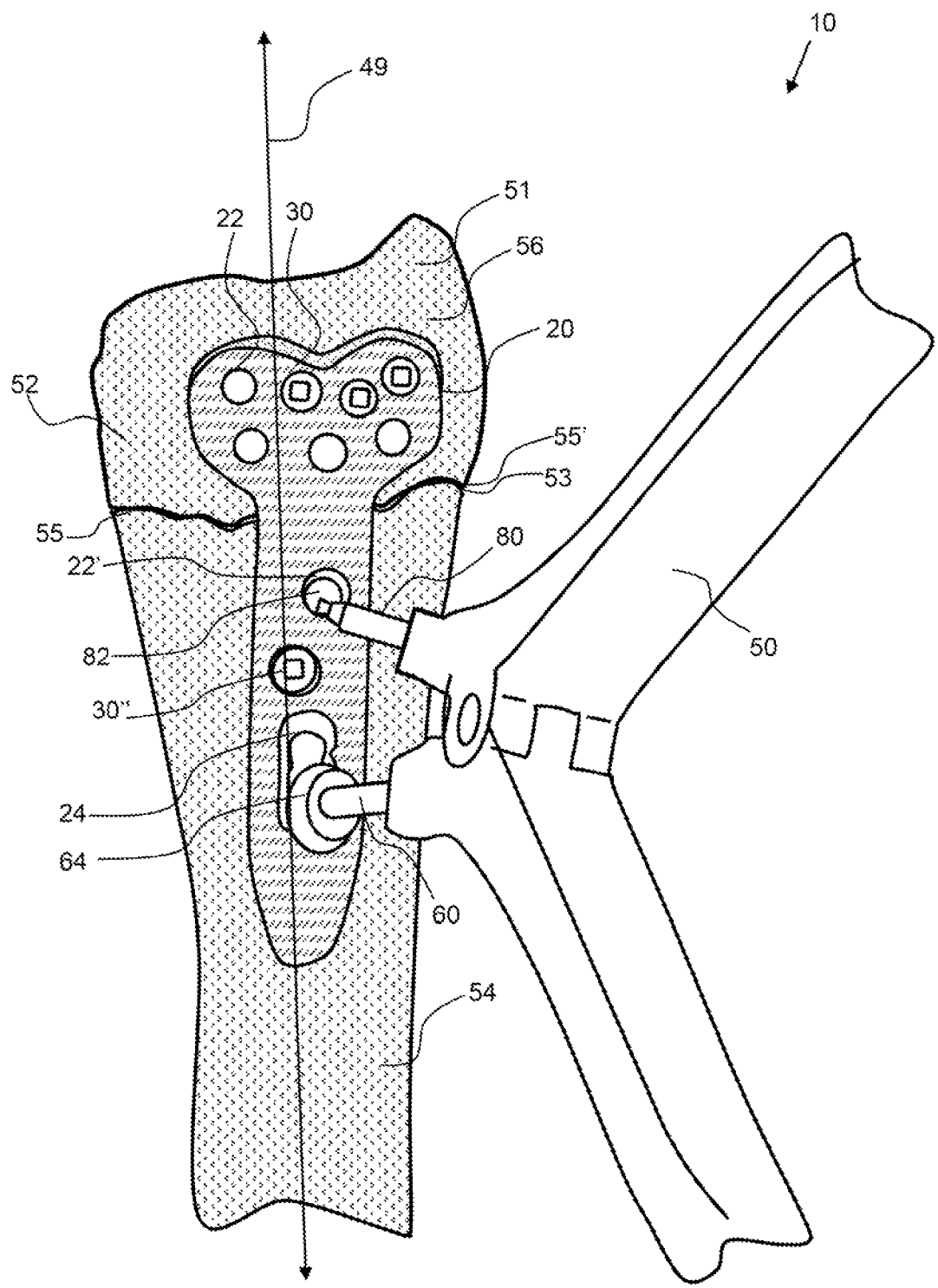

As shown in FIGS. 11 and 12, an exemplary bone manipulator system 10 comprise a bone manipulator 50 that can engage with a bone plate 20 to translate a displaced fractured bone to in two degrees of motion, axially and laterally. As shown in FIG. 11, a fracture bone is displaced to produce a fracture gap 55 and a lateral displacement 48, whereby the lateral displacement that is an offset that is orthogonal to the length axis 49 of the bone. The length axis is a line extending along the length of the bone portion that is closest to the correct anatomical position. When a small portion of the bone is fractured from a much larger or longer portion of the bone, the length axis extends along the length of the larger portion of the fractured bone. The exemplary bone manipulator may be used to translate the fractured bone back into a more anatomically correct position which may include movement of the bone fracture portion both laterally and along the length axis of the bone, as indicated by the two bold arrows in FIG. 11. One or more fasteners 30 may be configured through apertures 22 in the bone plate 20 and secured into the second bone portion 56 of the fractured bone 52, this being fractured bone portion. The domed coupler 64 of the fastener-arm 60 may be configured over a fastener 30' that extends through an aperture in the bone plate and into the first portion 54 of the fracture bone. The flared foot end 82 of the foot-arm 80 may be configured in a second aperture of the bone plate which is located toward the fracture from the slotted aperture. The second aperture may be more proximal to the fracture than the domed coupler 64 but over the first bone portion 54. The bone manipulator can be rotated and the flared foot end can be moved axially to manipulate the second bone portion 56, or the fracture bone portion 51, with respect to the first bone portion 54 to reduce the facture gap and move the bone fracture laterally. A fastener 30" may be inserted through an aperture in the first bone portion 54 to secure the manipulated fractured bone in position with respect to the bone plate, as shown in FIG. 12.

Figure 13:
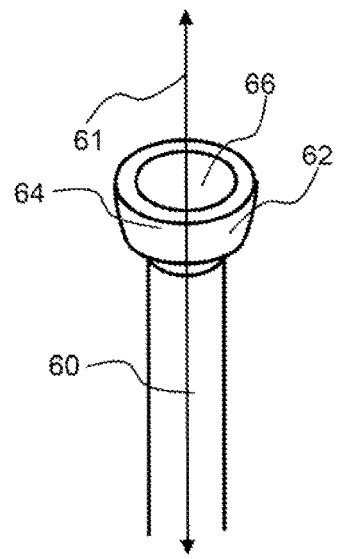
FIGS. 13, 14 and 15 show an exemplary fastener coupler of the bone manipulator.
Figure 14:
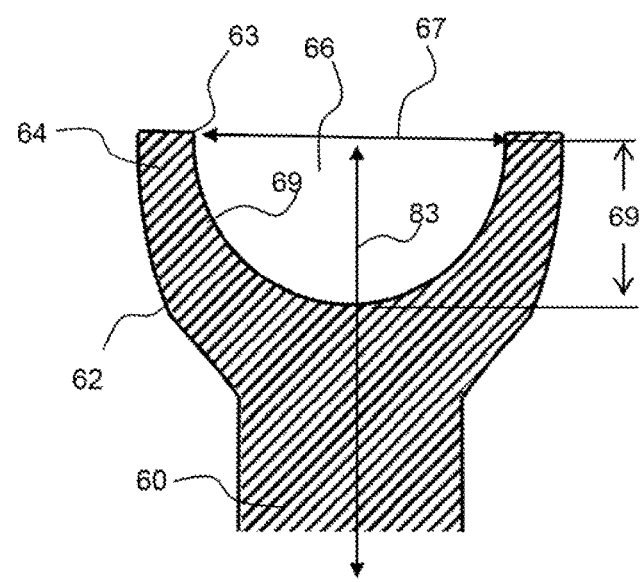
Figure 15:
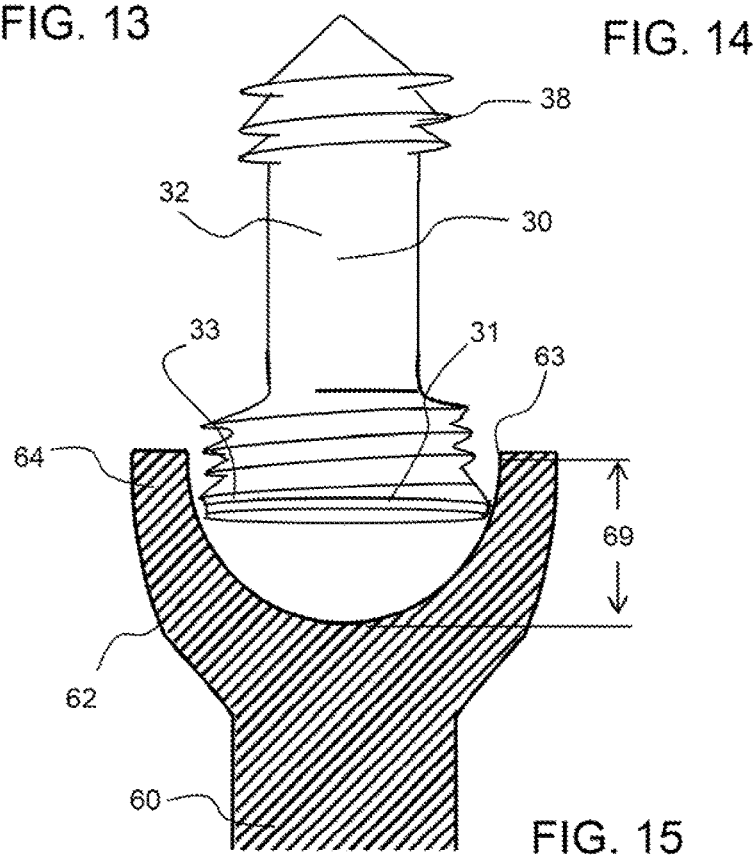

As shown in FIGS. 13 and 14, an exemplary fastener coupler 62 of the bone manipulator has a cavity 67 that may be dome shaped to extend around a fastener head 31 and allow secure engagement with the fastener during manipulation of the bone manipulator and in particular during rotation of the bone manipulator about the fastener. The domed coupler 64 may have a circular opening and a dome shaped cavity 66 as shown in FIG. 14 to allow the fastener head 31 to fit at least partially therein, whereby the opening perimeter 63 extends down beyond the top of the fastener head 33. The cavity has an opening diameter 67 that is larger than the diameter of a fastener and has a depth 69 to allow insertion of the fastener therein.

Figure 16:
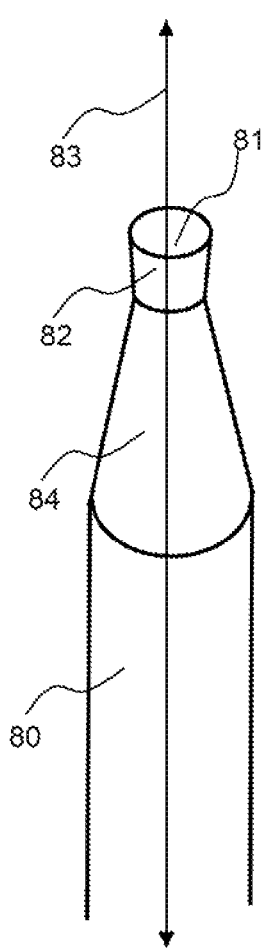
FIGS. 16 and 17 show an exemplary foot-arm of the bone manipulator having a flared foot end.
Figure 17:
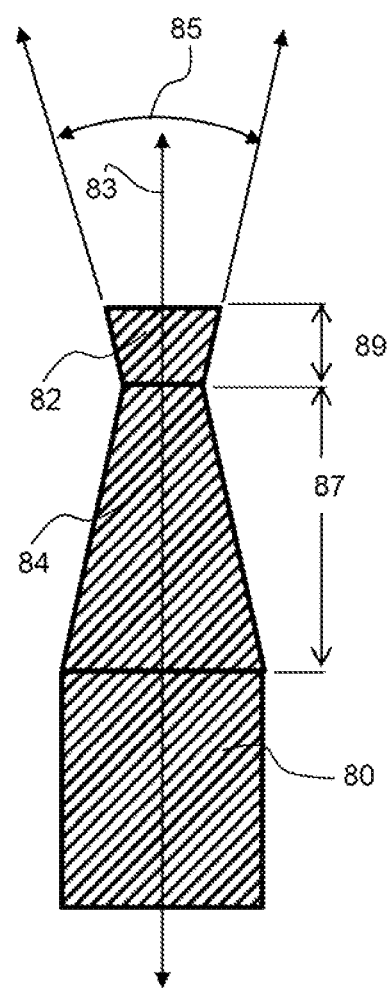

As shown in FIGS. 16 and 17, an exemplary foot-arm 80 of the bone manipulator has a flared foot end 82. The flared foot end enables the extended end 81 of the flared foot-arm to be secured between the bottom of the bone plate and the bone. The flared foot-arm has a tapered portion 84 having a length 87 which allows for a wider angle of insertion into an aperture of a bone plate. The flared foot end 82 has a length 89 and a flared foot angle 85. The flared foot angle may be about 40 degrees or more, about 55 degrees or more, about 70 degrees or more, about 90 degrees or more and any range between and including the flared foot angles provided. If the flared foot angle is too large it may cause the flared foot to lift the bone plate from the bone which is not desired and a foot with no flare may make it difficult to secure the foot in position.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of manipulating a fractured bone comprising the steps of:
    a) providing the bone manipulator system comprising:
        i) a bone manipulator comprising:
            a fastener-arm comprising:
                a fastener coupler on an extended end of the fastener-arm wherein the fastener coupler has a cavity to extend over a fastener;
            a foot-arm comprising a flared foot end on an extend end of the foot-arm;
            wherein the fastener-arm and foot-arm extend from a coupler;
        a pair of handles that extend from the coupler,
    b) providing a bone plate having a plurality of apertures for receiving a fastener therethrough and into a bone to secure the bone plate to said bone;
    c) configuring the bone plate over a fracture of the fractured bone to extend from a first bone portion on a first side of the bone fracture to a second bone portion of a second side of the bone fracture;
    d) inserting a fastener through a first aperture of the plurality of apertures and into said fractured bone, wherein the fastener has a fastener head that extend from a top surface of the bone plate;
    e) placing the cavity of the fastener coupler over the fastener head;
    f) inserting the flared foot end into a second aperture of the plurality of apertures;
    g) manipulating the bone plate with respect to the fastener; and
        wherein the first and second apertures are configured over the first bone portion configured on the first side of a bone fracture and wherein the bone plate is secure to the second bone portion;
        wherein the bone fracture has a non-uniform fracture gap from a first end to a second end of the bone fracture to produce a fracture angle and to misalign the fractured bone;
        manipulating the bone plate with the flared foot end to rotate the second bone portion to reduce the fracture angle and align the fractured bone.

2. The method of manipulating a fractured bone of claim 1, further comprising the step of inserting a fastener through one of the plurality of apertures and into the first bone portion to secure the bone plate to both the first and second bone portions.

3. The method of manipulating a fractured bone of claim 1, wherein the first and second apertures are configured over the first bone portion configured on the first side of the bone fracture and wherein the bone plate is secure to the second bone portion;
    wherein the bone fracture has the fracture gap and a lateral displacement;
    manipulating the bone plate with the flared foot end to translate the second bone portion to reduce both the fracture gap and the lateral displacement and align the fractured bone.

4. The method of manipulating a fractured bone of claim 3, further comprising the step of inserting a fastener through one of the plurality of apertures and into the first bone portion to secure the bone plate to both the first and second bone portions.

5. The method of manipulating a fractured bone of claim 1, wherein a first aperture of the plurality of apertures is a slotted aperture configured on the first side of the bone fracture and wherein the second aperture is configured over the side second bone portion;
    spreading the flared foot end from the fastener end to distract a compressed bone region.

6. The method of manipulating a fractured bone of claim 5, further comprising the step of inserting a fastener through one of the plurality of aperture in the bone plate and into the second bone portion to secure the bone plate to both the first and second bone portions.

7. The method of manipulating a fractured bone of claim 1, wherein the first and second apertures are configured on the first side of the bone fracture and wherein the first aperture is more proximal to the bone fracture than the second aperture;
  securing the bone plate to the second bone portion;
  spreading the flared foot end from the fastener end to reduce the fracture gap of the bone fracture.

8. The method of manipulating a fractured bone of claim 7, further comprising the step of inserting a fastener through one of the plurality of aperture in the bone plate and into the first bone portion to secure the bone plate to both the first and second bone portions.

\* \* \* \* \*